(12) United States Patent
Okamura et al.

(10) Patent No.: US 7,684,943 B2
(45) Date of Patent: Mar. 23, 2010

(54) PROBE CARRIER MANAGEMENT METHOD, PROBE CARRIER MANUFACTURING APPARATUS AND PROBE CARRIER MANAGING APPARATUS

(75) Inventors: Nobuyuki Okamura, Kanagawa (JP); Makoto Kameyama, Chiba (JP); Tadashi Okamoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/687,946

(22) Filed: Mar. 19, 2007

(65) Prior Publication Data
US 2007/0160505 A1    Jul. 12, 2007

Related U.S. Application Data

(62) Division of application No. 10/105,312, filed on Mar. 26, 2002, now Pat. No. 7,216,042.

(30) Foreign Application Priority Data
Mar. 28, 2001    (JP)    ............................. 2001-094366

(51) Int. Cl.
*G06F 19/00*    (2006.01)
(52) U.S. Cl. ............................ 702/67; 702/31; 422/63; 422/67; 422/100; 436/43; 436/46; 436/180
(58) Field of Classification Search ................ 702/19, 702/21–23, 25, 27, 30–32, 50, 183; 422/63–67, 422/100; 436/43, 45, 47–48, 46, 180
See application file for complete search history.

(56) References Cited

U.S. PATENT DOCUMENTS

| | | | |
|---|---|---|---|
| 5,004,582 A | 4/1991 | Miyata et al. | |
| 5,262,049 A | 11/1993 | Ferkany | |
| 5,798,085 A * | 8/1998 | Seaton et al. | ................. 422/65 |
| 5,846,491 A | 12/1998 | Choperena et al. | |
| 5,853,666 A | 12/1998 | Seaton et al. | |
| 5,869,006 A | 2/1999 | Fanning et al. | |
| 5,876,926 A * | 3/1999 | Beecham | ....................... 435/5 |
| 5,965,361 A | 10/1999 | Kigawa et al. | |
| 6,024,921 A | 2/2000 | Freiner et al. | |
| 6,176,119 B1 | 1/2001 | Kintzig | |
| 6,599,476 B1 | 7/2003 | Watson et al. | |
| 6,617,583 B1 * | 9/2003 | Bawendi et al. | ........ 250/370.01 |
| 6,685,884 B2 | 2/2004 | Stylli et al. | |
| 6,838,051 B2 * | 1/2005 | Marquiss et al. | .............. 422/63 |
| 6,953,551 B2 | 10/2005 | Chen et al. | |
| 7,216,042 B2 * | 5/2007 | Okamura et al. | .............. 702/31 |

(Continued)

*Primary Examiner*—Eliseo Ramos Feliciano
*Assistant Examiner*—Mary C Baran
(74) *Attorney, Agent, or Firm*—Fitzpatrick, Cella, Harper & Scinto (57) ABSTRACT

A method for appropriately managing the quality and distribution of a probe carrier. Probe carriers manufactured by a probe carrier manufacturing apparatus having ejecting portions for ejecting probe solutions, each containing a probe, which can be specifically coupled with a target substance, for applying the probe solution on a carrier, and a plurality of probe tanks storing mutually different probe solutions for supplying ejecting portions. Each probe tank is labeled with the bar-code. The labeled bar-code is read by the bar-code reader. On the basis of the read bar-code, the probe solution stored in the probe tank is identified. On the other hand, the probe tank is mounted on the ejecting portion.

19 Claims, 11 Drawing Sheets

U.S. PATENT DOCUMENTS

2001/0051714 A1    12/2001   Chen et al.
2002/0135632 A1*    9/2002   Tsuruoka .................... 347/19
2002/0142341 A1    10/2002   Kameyama et al.
2002/0146815 A1    10/2002   Watanabe et al.
2002/0180475 A1    12/2002   Watanabe et al.

* cited by examiner

PROBE CARRIER MANAGEMENT METHOD, PROBE CARRIER MANUFACTURING APPARATUS AND PROBE CARRIER MANAGING APPARATUS

This application is a division of application Ser. No. 10/105,312, filed Mar. 26, 2002, which is based on Japanese Patent Application No. 2001-094366, filed Mar. 28, 2001. Both prior applications are incorporated herein by reference.

BACKGROUND OF THE INVENTION

1. Field of the Invention

The present invention relates to a probe carrier managing method, a probe carrier manufacturing apparatus and a probe carrier managing apparatus.

2. Description of the Related Art

A probe, which can specifically couple with a target substance of a specific base sequence, such as a short single-stranded DNA strip and the like tagged by radioactive isotopes or other fluorescent materials, has been used for gene examination or analysis of a base sequence of gene DNA. As means for providing a plurality of kinds of probes simultaneously, probe carriers, such as a DNA chip prepared by arraying a plurality of probes to be coupled with target substances as objects for detection on a carrier of glass and the like or other carrier, are attracting attention.

In the recent years, studies have progressed in the area of applying technology relating to an ink-jet printer to the manufacturing of the probe carrier to enable to fix tens of thousands of probes on a single probe carrier. While the ink-jet printer places ink at accurate positions on a printing medium by ejecting droplets having a trace amount of ink, a high-density probe carrier can be manufactured by injecting a solution containing the probe in place of the ink in one operation.

When manufacturing the probe carrier, probes have to be fixed on the chip in a desired arrangement. However, there is a problem in that it is difficult or even impossible to constantly maintain an accurate arrangement of tens of thousands of probes.

On the other hand, when the probe carrier, such as a DNA chip and the like, is commercialized and placed on the market, it is possible for the probe carrier to fail after manufacturing, but before use, during distribution. A failure may be caused by:

(1) taking the wrong probe in the manufacturing stage, alternation of the probe or mixing of a plurality of probes;

(2) alternation of the probe in the distribution stage; and (3) misidentification of the result of the inspection during the inspection stage. Other causes may also be possible. However, while the failure of the probe carrier is normally found during the inspection stage, the cause of the failure cannot be specified unless appropriate management is exercised.

SUMMARY OF THE INVENTION

An object of the present invention is to provide a management method of a probe carrier, a probe carrier manufacturing apparatus and a probe carrier managing apparatus, which permits appropriate management of quality and distribution of the probe carrier.

To attain this object, a first aspect of the present invention provides a management method of probe carriers employing a probe carrier managing apparatus having an indicator reading device for managing probe carriers manufactured by a probe carrier manufacturing apparatus, which has ejecting portions for ejecting the probe solutions, each containing a probe, which can be specifically coupled with a target substance, for application of the probe solutions on carriers for producing probe carriers, and a plurality of containers for accommodating mutually different probe solutions to be supplied to the containers, the containers respectively labeled with indicators. The probe carrier managing apparatus performs steps of reading the indicators on the plurality of containers according to a predetermined order by the reading device, comparing information about a plurality of the read indicators with information about a plurality of indicators stored in a storage device in a predetermined order and notifying the result of comparison.

The plurality of containers may be mounted in the ejecting portions. The plurality of containers may be formed in a predetermined arrangement. The indicator may be a bar-code.

A second aspect of the present invention provides a management method of probe carrier for managing probe carriers labeled with indicators, using a probe carrier managing apparatus, comprising the steps of storing the indicator and information relating to each probe carrier labeled with the indicator with correspondence therebetween in a storage device, receiving information about the indicator from outside and extracting information relating to the probe carrier corresponding to the received information about the indicator, from the storage device.

The method of managing a probe carrier may further comprise a step of transmitting at least one information relating to the indicator and the probe carrier stored in the storage device in response to an externally received demand.

Also, the method of managing a probe carrier may further comprise the steps of reading the indicator on the probe carrier using the reading device and extracting information relating to the probe carrier corresponding to information about the read indicator from the storage device. The indicator may be a bar-code.

A third aspect of the present invention provides a probe carrier manufacturing apparatus comprising ejecting portions for ejecting a probe solutions, each containing a probe, which can be specifically coupled with a target substance, for applying the probe solutions on a carrier for producing a probe carrier and a plurality of containers for accommodating mutually different probe solutions for supplying to the ejecting portions, each of the containers being labeled with indicators to identify the accommodated probe. The plurality of containers may be mounted on the ejecting portions. The plurality of containers may be formed in a predetermined arrangement. The indicator may be a bar-code.

A fourth aspect of the present invention provides a probe carrier managing apparatus for managing a probe carrier manufactured using the probe carrier manufacturing apparatus comprising a storage means for storing a plurality of the indicators in a predetermined order, a reading means for reading the indicators labeled on the plurality containers according to a predetermined order, a comparing means for comparing information about a plurality of the read indicators and information about a plurality of indicators stored in the storage means and a notifying means for notifying the result of the comparison made by the comparing means.

A fifth aspect of the present invention provides a probe carrier managing apparatus for managing a probe carrier labeled with an indicator, comprising a storage means for storing the indicator and information relating to probe carrier labeled with the indicator, a receiving means for externally receiving the indicator and an extracting means for extracting information relating to a probe carrier corresponding to information about the received indicator from the storage means.

A sixth aspect of the present invention provides a method of comparing information about probe carriers, comprising the steps of providing a solution applying apparatus having a plurality of liquid applying units for applying solutions on a carrier, wherein each of the solutions includes a probe, which can be specifically coupled with a target substance, a plurality of containing units for containing the solutions to be provided to each of the liquid applying units and a plurality of indicators for identifying types of the solutions in the containing units, obtaining information about the types of the plurality of solutions to be applied by the solution providing apparatus on the carrier based on the indicators, obtaining predetermined information about the types of the solutions to be applied on the carrier and determining whether the predetermined information matches the information based on the indicators.

The method of comparing information about probe carriers may further comprise the step of changing the solutions in the containing units when the predetermined information does not match the information based on the indicator.

With the present invention, a failure that occurred during production of the probe carrier can be prevented. As a result, appropriate quality control can be performed.

On the other hand, the probe carrier manufacturer used in the present invention has the head unit in which the probe tank is mounted on the ejecting portion. Thus, the probe carrier manufacturer can perform quality control of the probe carrier per head unit.

Furthermore, with the present invention, the arrangement of the probe array consisting of a large number of different kinds of probes fixed on the probe carrier can be easily managed.

The above and other objects, effects, features and advantages of the present invention will become more apparent from the following description of embodiments thereof taken in conjunction with the accompanying drawings.

DETAILED DESCRIPTION OF PREFERRED EMBODIMENTS

In the present invention, the probes fixed to the substrate are specifically associable to specific target substances. In the embodiment of the present invention, the target substances are nucleic acids, and the probes are mono-strand nucleic acids, which have a complementary base sequence to the whole or part of the target nucleic acid, so that the probes can specifically hybridize with the base sequence of the target nucleic acids. Further, the probes include oligonucleotides, polynucleotides, and other polymers that can recognize specific targets. The term "probe" means both individual molecules having probe functions, such as polynucleotide molecules, and a mass of molecules having the same probe functions fixed on the surface at separate positions, such as polynucleotides with same sequences, often including so-called ligands. Further, probes and targets are often exchangeably used, and the probes are substances either associable to targets as parts of ligand-antiligand (sometimes called receptor) pairs or changeable to substances that associate thereto. The probes and targets in the present invention can include bases found in nature and similar substances.

Examples of probes held on the substrate include oligonucleotides having base sequences hybridizable to target nucleic acids and having a bonding part to the substrate via linkers, the probe having structures connected to the surface of the substrate in the bonding part. The probe is preferably a mono-strand nucleic acid, which has a base sequence complementary to all or a part of target nucleic acid and can hybridize specifically with the target nucleic acid. Further, in such a configuration, the positions of the bonding part to the substrate in the oligonucleotide molecules are not limited as long as the desired hybridization reaction is not damaged.

The probes adopted in the probe carriers manufactured by the method of the present invention are appropriately selected according to their purpose of use. In order to implement the method of the present invention appropriately, the probes are preferably DNAs, RNAs, cDNAs (complementary DNAs), PNAs, oligonucleotides, polynucleotides, other nucleic acids, oligopeptides, polypeptides, proteins, enzymes, substrates for enzymes, antibodies, epitopes for antibodies, antigens, hormones, hormone receptors, ligands, ligand receptors, oligosaccharides, or polysaccharides, of which two or more can be used in combination if necessary.

In the present invention, plural kinds of these probes fixed on the separate regions (such as dot-shaped spots) of the surface of the substrate (including internal surfaces of hollow or ring-shaped carriers) are called "probe carrier", and those arranged at determined intervals are called "probe array".

It is desirable that probe materials have structures bondable to the solid phase substrate and that they are bonded to the solid phase substrate utilizing such bondable structures after ejection and application of probe solutions. The structures bondable to the solid phase substrate can be formed by introducing organic functional groups, such as amino, mercapto, carboxyl, hydroxyl, acid halide (—COX), halogen, aziridine, maleimide, succinimide, isothiocyanate, sulfonyl chloride (—SO$_2$Cl), aldehyde (—CHO), hydrazine, and iodoaceatamide groups, into the probe material molecules in advance. In that case, it is also necessary to introduce structures (organic functional groups) onto the surface of the substrate in advance, which structures form covalent bonds by reacting with the various functional groups described above. For example, when the probe material has amino groups, a succinimide ester, an isothiocyanate, a sulfonyl chloride, or an aldehyde can be introduced on the surface of the substrate. When the probe material has mercapto (thiol) groups, a maleimide can be introduced on the surface of the substrate. When a glass substrate is used as the substrate, desired functional groups can be introduced on the surface thereof using a silane coupling agent having desired functional groups, as well as a cross-linker having desired functional groups.

Hereinafter, embodiments of the present invention will be discussed in detail with reference to the drawings.

First Embodiment

Figure 1:
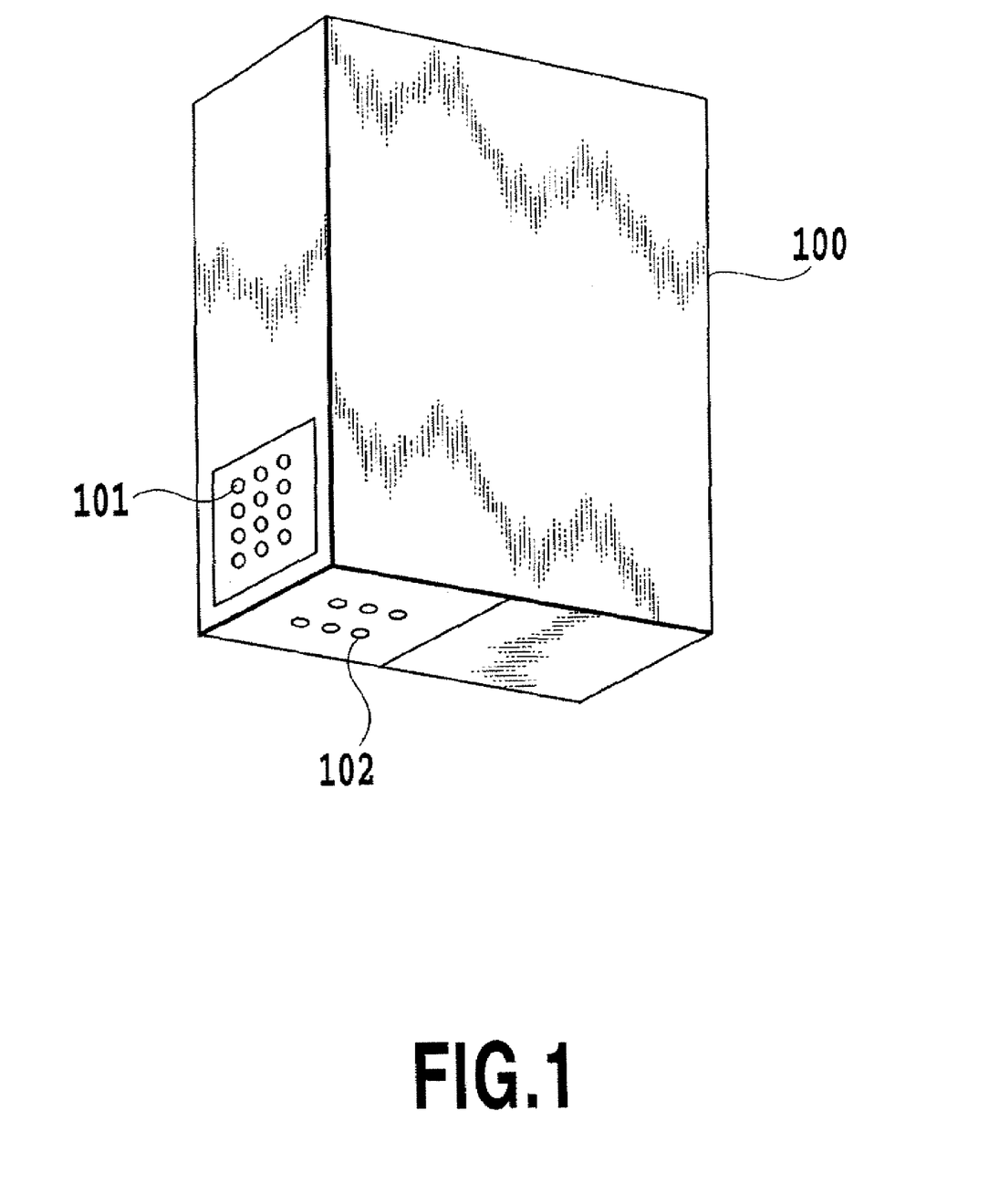
FIG. 1 is a perspective view of a probe tank provided in a probe carrier manufacturing apparatus, to which the present invention is applied.
Figure 2:
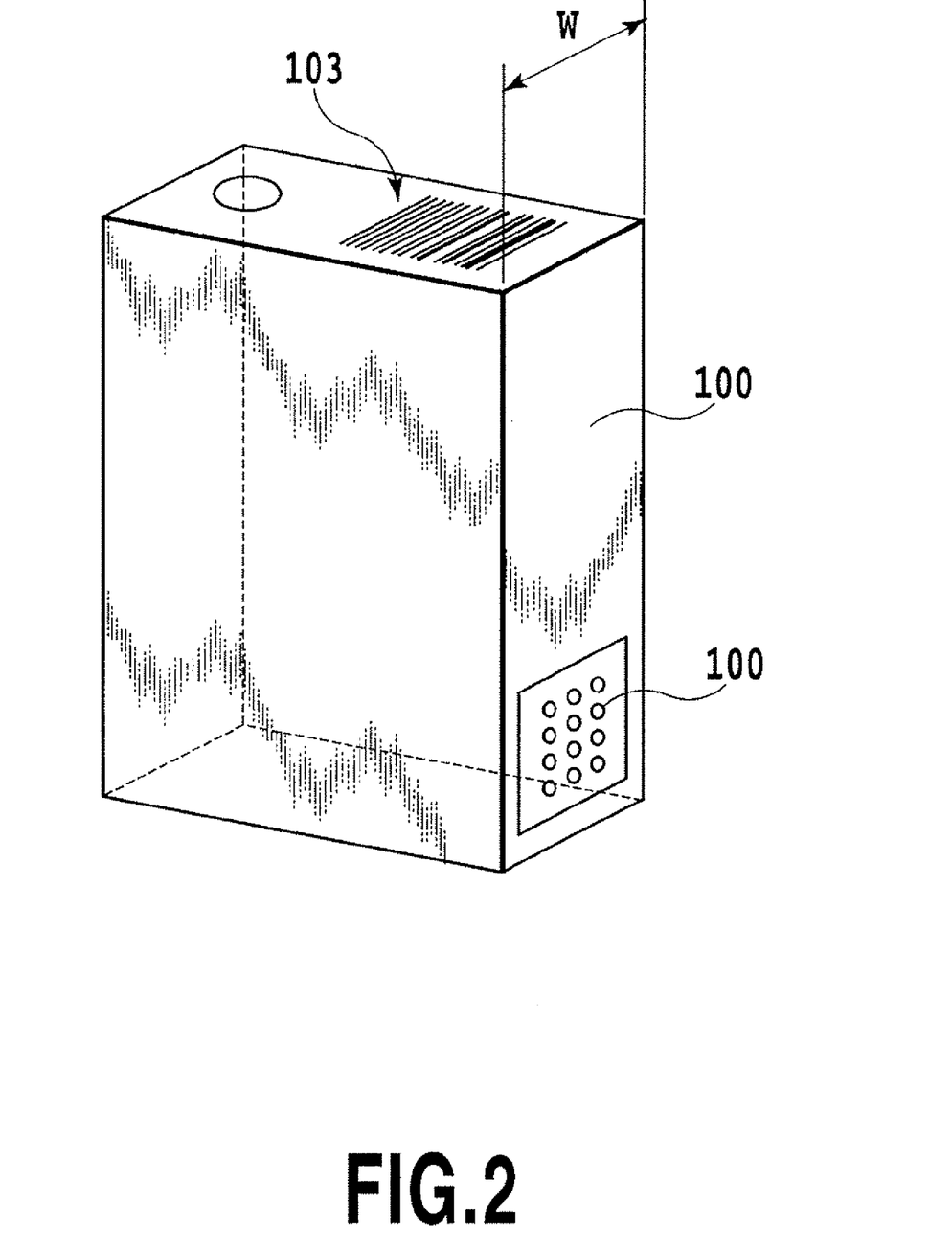
FIG. 2 is a perspective view of the probe tank provided in a probe carrier manufacturing apparatus, to which the present invention is applied.

FIGS. 1 and 2 are perspective views showing schematic configurations of probe tanks incorporated in a probe carrier manufacturing apparatus, to which the present invention is applied. One probe tank 100 is a container storing a solution containing a probe consisting of one kind of a base sequence (probe solution) therein, which corresponds to an ink tank in the conventional inkjet printer. The configuration is similar to the conventional ink tank and is to heat a heater (not shown) by a current externally applied to an electrical contact 101 for ejecting the probe solution stored in the probe tank through a nozzle 102.

On the other hand, as shown in FIG. 2, on an upper portion of the probe tank 100, a bar-code 103 as an indicator for identifying a kind of the probe is provided.

Figure 3:
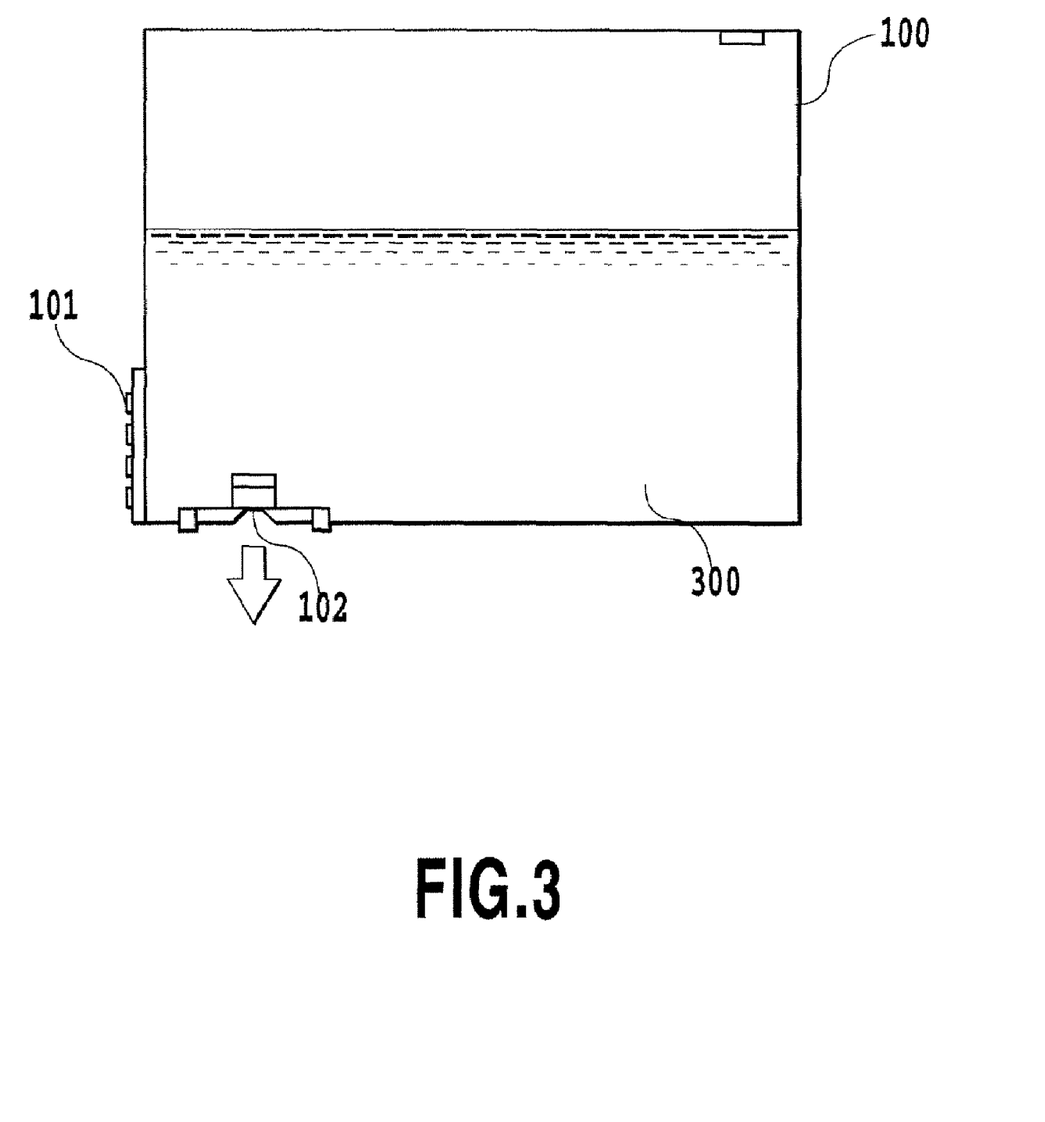
FIG. 3 is a side elevation of the probe tank provided in a probe carrier manufacturing apparatus, to which the present invention is applied, which illustrates a side wall as transparent to show the inside of the probe tank.

FIG. 3 is a side elevation of the probe tank provided in a probe carrier manufacturing apparatus, to which the present invention is applied, which illustrates a side wall as being transparent to show the inside of the probe tank. As shown in FIG. 3, a probe solution 300 stored in the probe tank 100 is heated by a heater (not shown) to be ejected through a nozzle 102 in the direction of arrow A.

Figure 4:
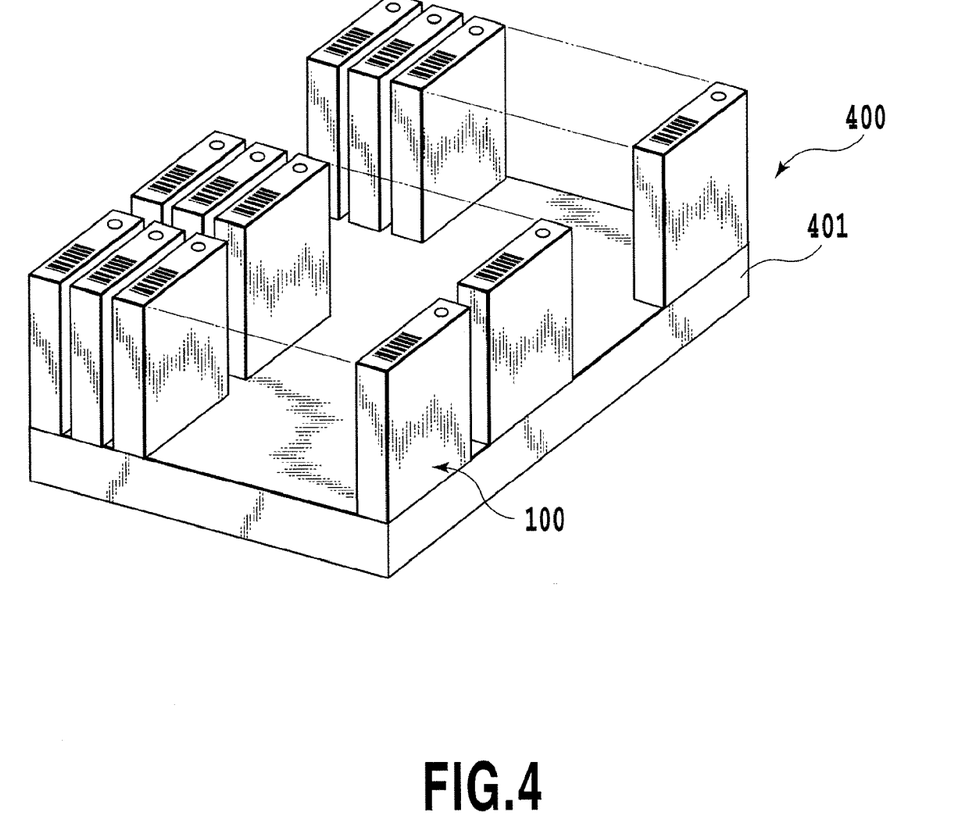
FIG. 4 is a perspective view showing a schematic configuration of a head unit provided in the probe carrier manufacturing apparatus, to which the present invention is applied.

FIG. 4 is a perspective view showing a schematic configuration of a head unit of the probe carrier manufacturing apparatus to which the present invention is applied. A head unit 400 has an ejecting portion 401 corresponding to a head printing portion in the conventional inkjet printer and the probe tanks 100 mounted on the ejecting portion 401 and arranged in a predetermined two-dimensional arrangement. Each of probe tanks 100 stores probe solutions respectively containing probes consisting of DNAs having mutually different base sequences.

A probe carrier manufacturer prepares a plurality of probe tanks storing mutually different probe solutions, selects probe tanks depending upon demand from a customer and assembles a head unit by mounting the selected probe tank on an ejecting portion. In the alternative, a plurality of head units forming mutually different probe array are prepared and a desired head unit is selected upon manufacturing the probe carrier.

Figure 5:
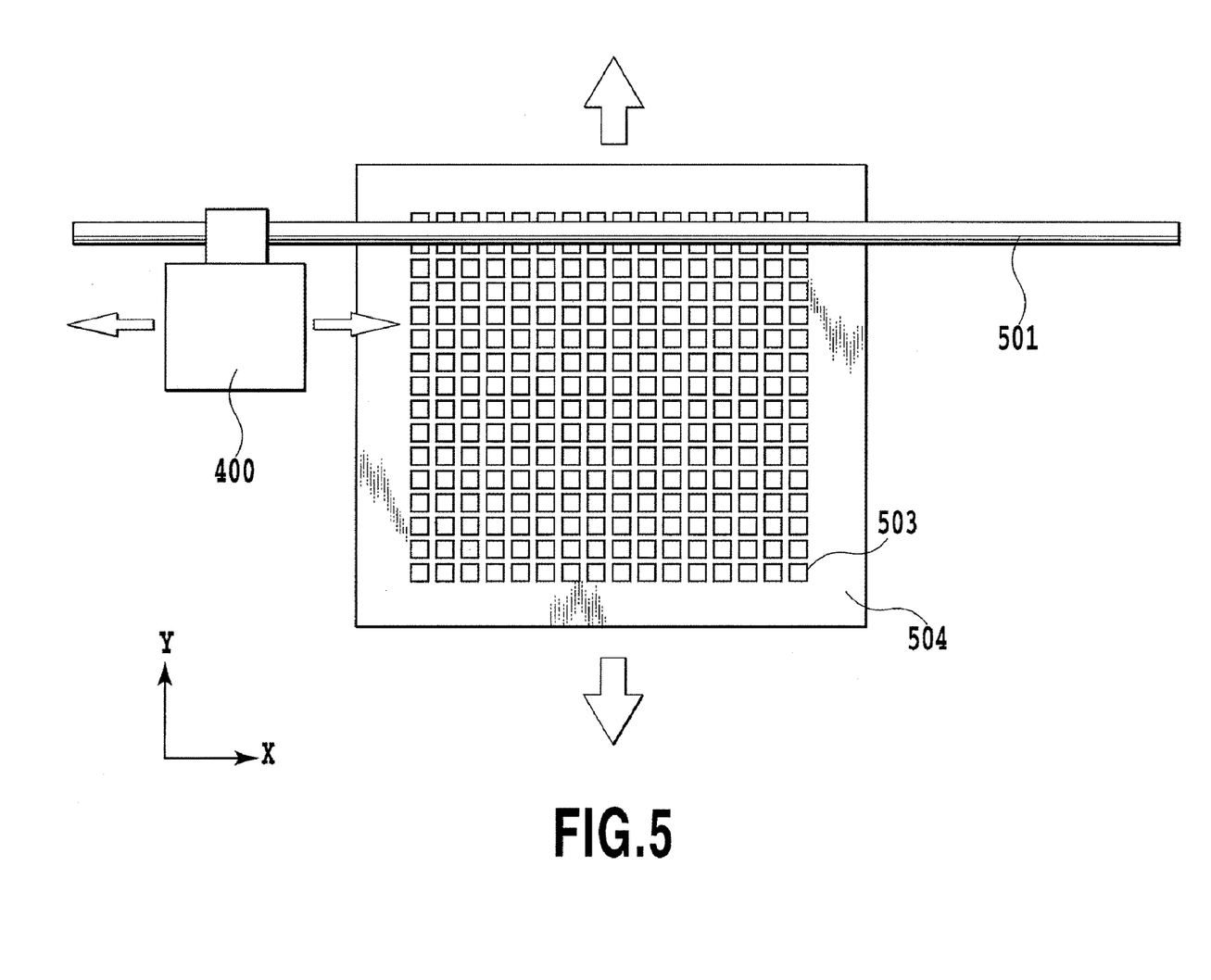
FIG. 5 is a diagrammatic illustration showing a configuration of the major portion of the probe carrier manufacturing apparatus using the head unit shown in FIG. 4.

FIG. 5 is a diagrammatic illustration showing a configuration of the major portion of the probe carrier manufacturing apparatus using the head unit shown in FIG. 4. In FIG. 5, the head unit 400 is supported on a shaft 500. On the other hand, a plurality of carriers 503 respectively formed with probe arrays are fixed on a stage 504. In the shown embodiment, a glass substrate is premised as the carrier 503.

The head unit 502 moves in the X-axis direction in FIG. 5, namely in a primary scanning direction as guided by the shaft 501. On the other hand, the stage 504 is moved in the Y-axis direction, namely in an auxiliary scanning direction. By these operations, the head unit 400 may move in a two-dimensional direction relative to the stage 504. It should be noted that while a configuration in the case where a plurality of glass substrates are fixed on the stage to apply the probe is in the foregoing discussion in connection with FIG. 5, it is also possible to eject the predetermined probe solution on a carrier formed with a large, single glass plate, and subsequently to cut the carrier to obtain respective probe arrays.

Figure 6:
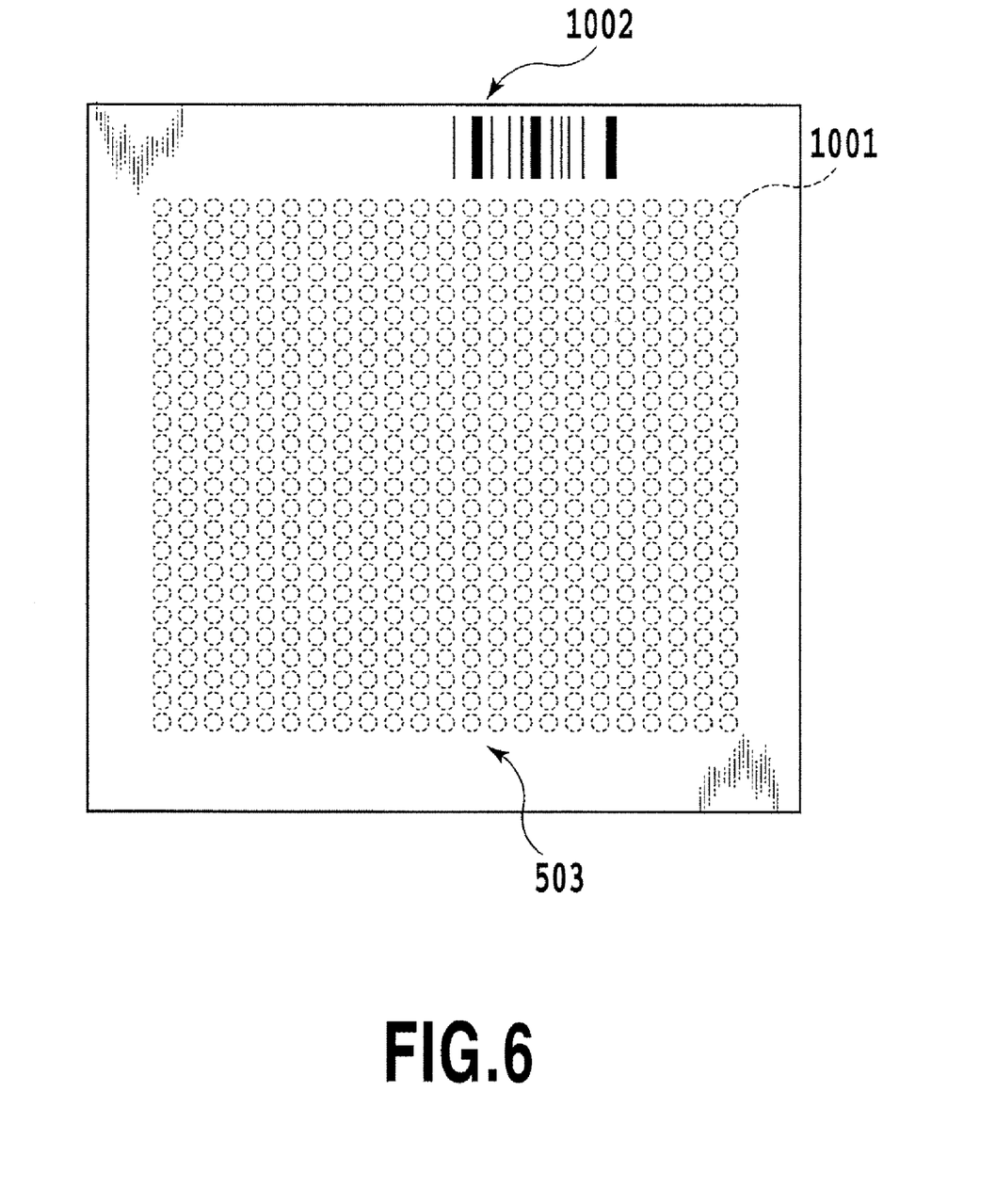
FIG. 6 is an illustration showing a schematic configuration of one probe carrier.

FIG. 6 shows one carrier, namely the probe carrier fixed on the stage 504 shown in FIG. 5. On the carrier 503, a plurality of holes (well) 1001 ejecting the probe solution of one kind of a base sequence are arranged in two-dimensional array, and a bar-code 1002 is printed as an indicator for identifying respective carrier 503.

Figure 7:
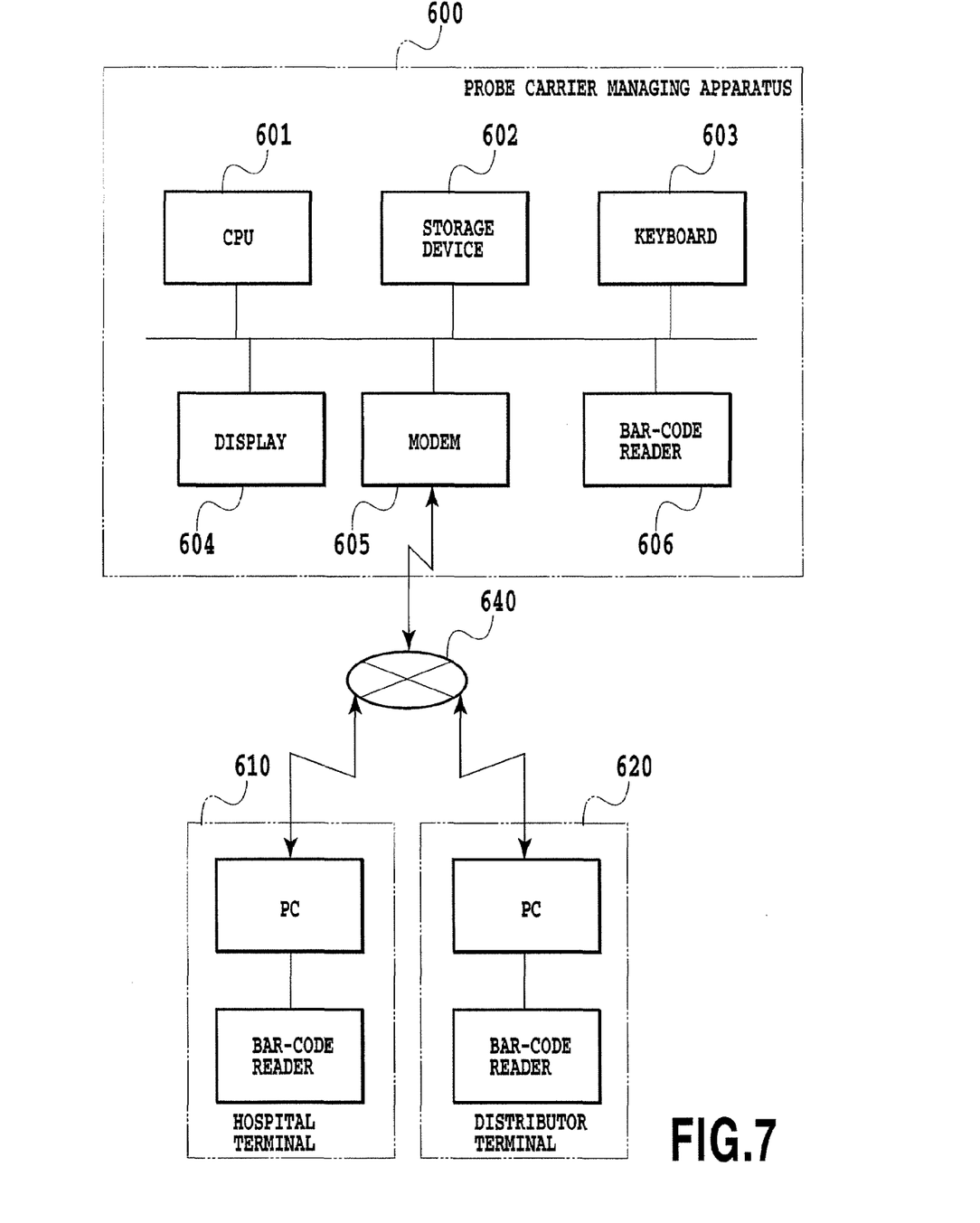
FIG. 7 is an illustration showing a system configuration for managing the probe carrier.

Next, with reference to the configuration of FIG. 7, a configuration will be described for a system managing the probe carrier manufactured by the foregoing probe carrier manufacturing apparatus. In FIG. 7, a probe carrier managing apparatus 600 is a server for managing entities manufacturing the probe carrier (hereinafter referred to as probe carrier manufacturer) using the foregoing probe carrier manufacturing apparatus. The server includes a modem 605 for connecting to the Internet 640 as a communication network, a display 604 displaying an image, a central processing unit (CPU) controlling the entire probe carrier managing apparatus, a keyboard 603 for inputting data, a storage device 602, such as a hard disk and a bar-code reader 606 as a reading device for reading the bar-code.

In the storage device 602, an aggregate of the bar-code data of the probe tanks and information relating to probes stored in the probe tanks are stored in a form of a database. On the other hand, in the storage device 602, programs for executing processes relating to the present invention are stored. CPU 601 provided in the computer reads out and executes a program code stored in the storage device to realize the present invention.

A hospital terminal 610 is an information processing unit installed in a hospital performing a gene examination using the probe carrier, and a distributor terminal 620 is an information processing unit installed in a distributor performing a distribution of the probe carrier. All of these information processing units include personal computers (PCs) having communication interfaces for connecting with the Internet 640 and a bar-code reader, respectively.

In the shown embodiment of the system, the hospital terminal 610, the distributor terminal 620 and the probe carrier managing apparatus 600 are connected through the Internet 640. Therefore, the hospital terminal 610 and the distributor terminal 620 may access the probe carrier managing apparatus 600 to obtain information stored in the storage device 602 and transmit information input to respective terminals.

Next, one example of the process of the shown embodiment of the probe carrier management will be explained with reference to flowcharts shown in FIGS. 8 to 10.

Figure 8:
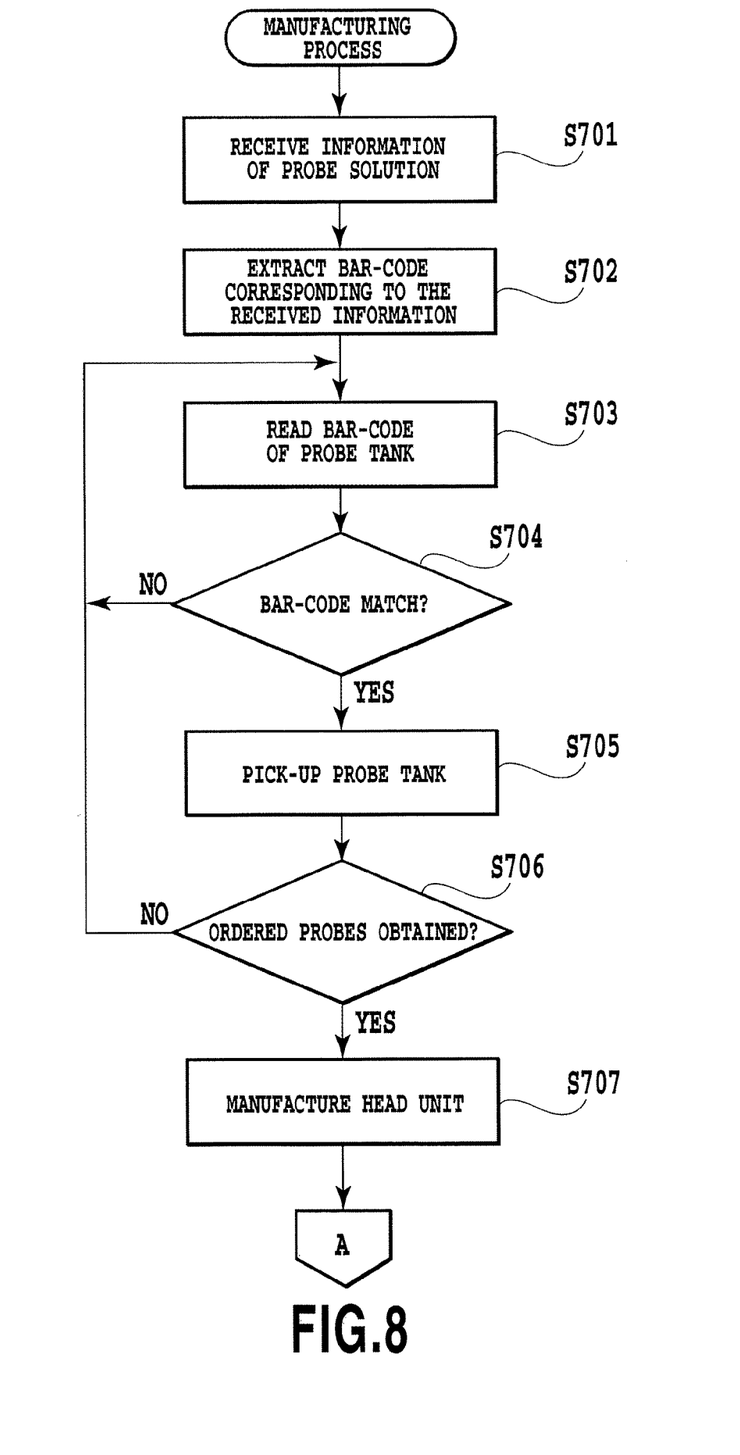
FIG. 8 is a flowchart showing a process of one embodiment of probe carrier management according to the present invention.
Figure 9:
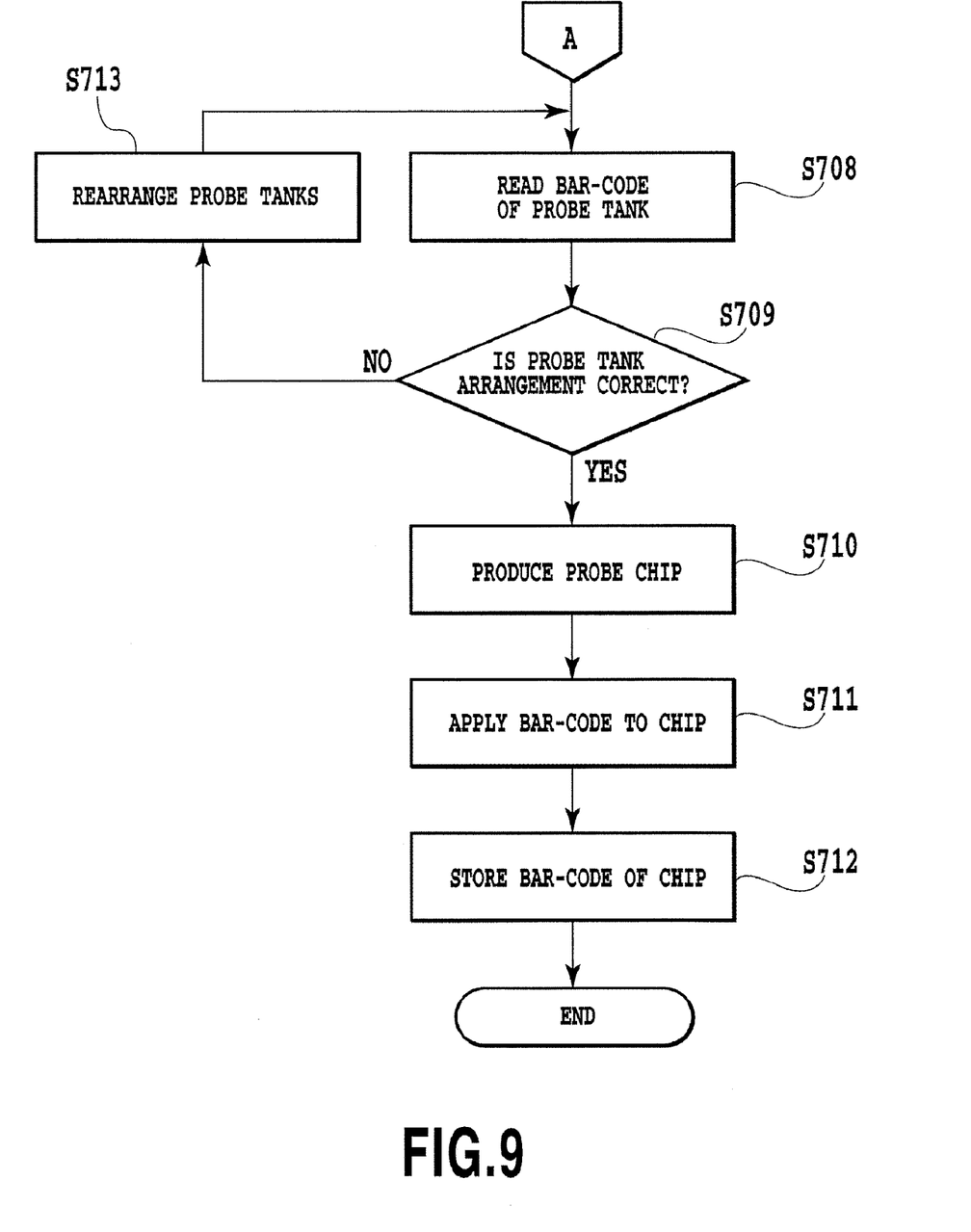
FIG. 9 is a flowchart showing a process of one embodiment of probe carrier management according to the present invention.

FIGS. 8 and 9 illustrate a process in the manufacturing stage. At first, the probe carrier managing apparatus 600 receives information relating to an order for the probe carrier from the hospital terminal 610 installed in the hospital as an orderer (step S701). In the information received here, information of a series of probes forming the probe carrier is contained in a predetermined order. The probe carrier managing apparatus 600 extracts bar-code data corresponding to probe contained in the received information from bar-code data in the database to temporarily store in the predetermined region of the storage device (step S702).

The probe carrier manufacturer selects one of a plurality of kinds of probe tanks, which are prepared preliminarily, and reads the bar-code labeled for the probe tank using the bardoe reader 606 of the probe managing apparatus 600 (step S703). The probe carrier managing apparatus 600 determines whether the bar-code data input via the bar-code reader 606 is contained in the bar-code data extracted at step S702 (step S704). When the bar-code data is contained in the extracted bar-code data, the probe carrier managing apparatus 600 displays an instruction on the display 604 that the selected probe tank is necessary for the production of the probe carrier. The probe carrier manufacturer obtains the selected probe tank as the probe tank for formation of the head unit on the basis of the display (step S705). Then, the process is advanced to step S706. When the bar-code data of the probe tank is not contained in the extracted bar-code data, the fact is displayed on the display. The probe carrier manufacturer returns to step S703 based on the display to repeat the reading process of the bar-code with selecting a new probe tank.

In step S706, the probe carrier managing apparatus 600 checks whether all probe solutions required for preparation of the ordered probe carrier are obtained. When all necessary probe tanks are obtained, the fact is displayed on the display 604. The probe carrier manufacturer mounts all obtained probe tanks on the ejecting portion to form the head unit (step S707). Then, the process is advanced to step S708 of FIG. 9. On the other hand, if all necessary probe tanks are not obtained, the process returns to step S703 to repeat from bar-code reading process.

In step S708 of FIG. 9, the probe carrier manufacturer reads the bar-code of the probe tank mounted on the head unit using the bar-code reader of the probe carrier managing apparatus 600 in the predetermined order. The probe carrier managing apparatus 600 compares the bar-code data obtained from the bar-code reader and a series of bar codes extracted in step S702 to verify that the probe tanks are in a predetermined arrangement. Then, the result of the comparison is displayed on the display to notify the probe carrier manufacturer (step S709). If the probe tank arrangement is incorrect, the probe tanks are rearranged (step S713) to repeat from step S708.

The probe carrier manufacturer assembles the formed head unit in the probe carrier manufacturing apparatus after verifying the correct arrangement of the probe tank on the basis of the notice in step S709 to produce the probe carrier (step S710). Next, for each probe carrier manufactured as above, the bar code for identifying the chip per se is written by a known method (step S711).

The manufacturer reads the bar-code written on the probe carrier using the bar-code reader 606. The probe carrier managing apparatus 600 stores data relating to the probe carrier, such as the read out bar-code, manufacturing date, delivery destination, data identifying arrangement of the probe array on the chip and so on with correspondence as an aggregate of data (database) (step S712).

Figure 10:
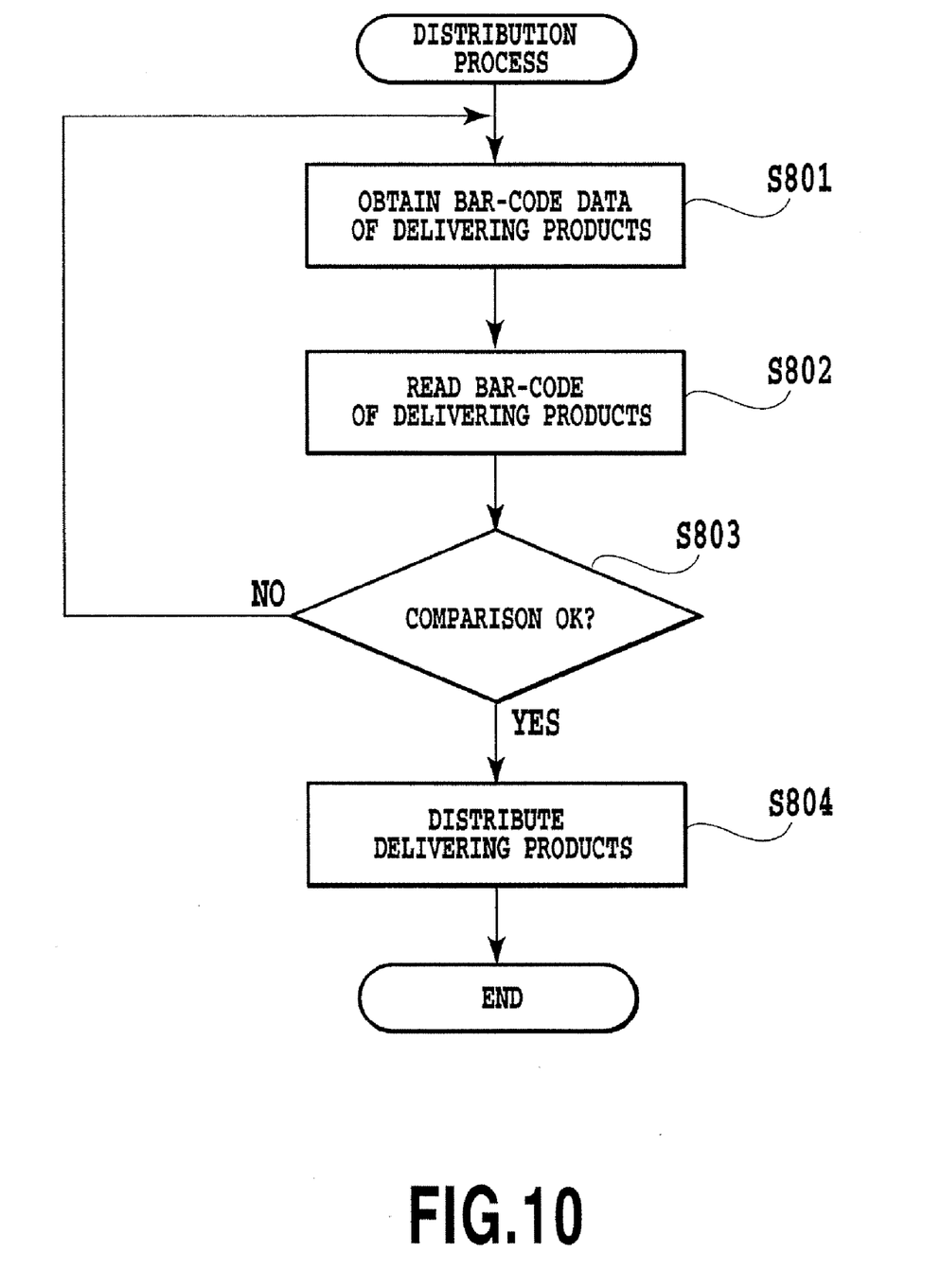
FIG. 10 is a flowchart showing a process of one embodiment of probe carrier management according to the present invention.

FIG. 10 shows a flowchart showing the process executed by the distributor in the distribution stage. In step S801, the distributor terminal 620 is used to demand information relating to delivering products to the probe carrier managing apparatus 600. The probe carrier managing apparatus 600 responds to the demand received from external distributor terminal 620 to transmit at least one piece of information relating to the bar-code data and probe carrier stored in the storage device. In step S802, the bar-code reader of the distributor terminal 620 is used to read out the bar-code attached to the delivering products. The distributor terminal 602 compares the read out data with the bar-code data obtained from the probe carrier managing apparatus 600 (step S803).

As a result of the comparison, when a discrepancy in barcode data is identified, the process is repeated from step S801. On the other hand, when all of read out bar-code data matches the data from the probe carrier managing apparatus, the verified products are delivered.

Figure 11:
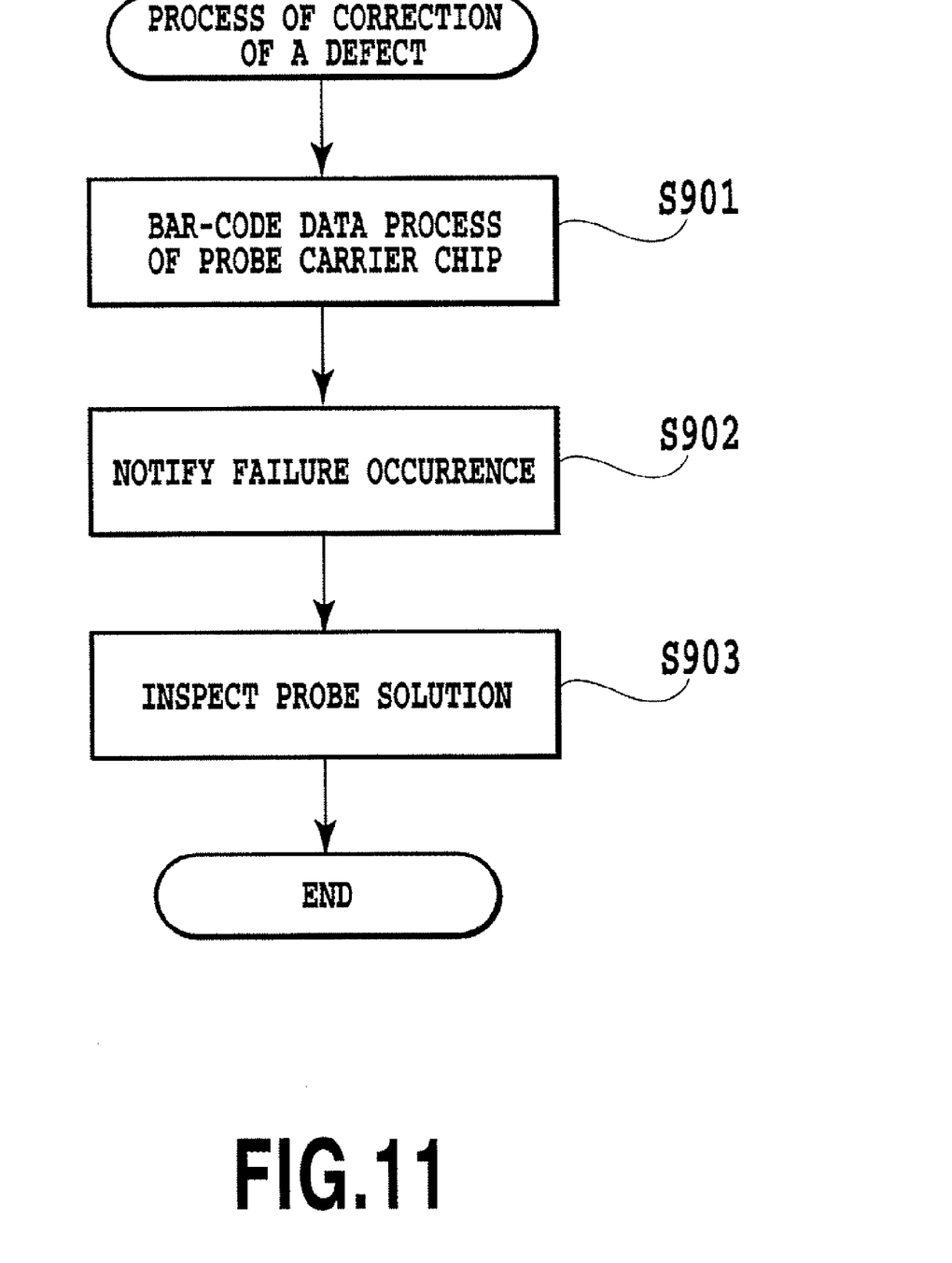
FIG. 11 is a flowchart showing a process of one embodiment of probe carrier management according to the present invention.

FIG. 11 is a flowchart showing a procedure to be executed by the probe carrier manufacturer when a failure in the probe carrier is detected in an inspection stage.

When a failure of the probe carrier is detected as a result of gene examination in the hospital, the bar-code of the probe carrier is read out using the bar-code reader provided in the hospital terminal 610, and the bar-code data read as above is transmitted to the probe carrier managing apparatus 600.

When the probe carrier managing apparatus 600 receives the bar-code of the imperfect probe carrier from the hospital terminal 610 (step S901), information regarding the manufacturing data, and so on, of the probe carrier corresponding to the bar-code is extracted from the database and is displayed to notify the probe carrier manufacturer of the failure (step S902). The probe carrier manufacturer identifies the head unit of the probe carrier manufacturer used upon manufacturing on the basis of the notified information to inspect the probe solution (step S903).

By performing such management of the probe carrier, the manufacturer can certainly form the desired arrangement of the probe tank. Also, false recognition of the delivering products in the distribution stage can be prevented. Also, even when a failure is caused in the probe carrier in the inspection stage, the failure of the probe carrier can be analyzed by the manufacturer. On the other hand, when the result of the analysis indicates that the probe carrier is normal, it may be predicted that a misidentification in the inspection stage or an alternation of the probe carrier, and so on, has occurred.

It is also possible to return the probe carrier from the hospital to the probe carrier manufacturer without sending the bar-code of the imperfect probe carrier from the hospital terminal. In this case, the manufacturer reads the bar-code of the returned probe carrier using the bar-code reader of the probe carrier managing apparatus 600 and analyze a cause of failure.

In addition to the embodiment set for the above, the present invention can be implemented in the following embodiment.

(1) In the hospital, re-inspection may be performed for the delivered products. In this case, the operator of the hospital terminal performs an inspection of the delivered products shown in the flowchart of FIG. 10.

(2) In the bar-code to be written on the probe tank and the probe carrier, information indicative of the manufacturer's identification information and the manufacturing date may be included.

(3) While the shown embodiment is an example where the bar-code is attached to each probe carrier after manufacturing of the probe carrier, it is also possible to prepare a stage preliminarily attached the bar-codes per the carrier to manufacture the probe carrier using such a stage.

(4) The information to be stored in the database of the probe carrier managing apparatus is not limited to that in foregoing embodiment. The database can store the results of the gene examination or the result of a measurement using the probe carrier, for example. In this case, the bar-code data of the probe carrier and the result of the inspection or the result of the measurement using the probe carrier is input into the hospital terminal in the hospital to transmit to the probe carrier managing apparatus. The probe carrier managing apparatus brings the received bar-code data into correspondence with the inspection result or the measurement result and stores the data and the result in the database. The inspection result or the measurement result of each probe carrier collectively stored can be used for quality control of the probe carrier by the prove carrier manufacturer, management of distribution step by the distributor, and so forth.

(5) A process of the probe carrier management is not limited to the procedure as illustrated in the flowcharts of FIGS. 8 to 11.

(6) It should be noted that when the liquid ejecting apparatus is used upon applying a liquid containing a probe, a sample, and so on, the liquid ejecting apparatus, in which liquid ejecting portions, each including a liquid containing portion, a nozzle to be connected to the liquid containing portion and to eject the liquid, a liquid ejection energy generating means for generating energy for ejecting the liquid from the nozzles, are provided in a required number, which depends upon the kind of the liquid to be ejected. As the liquid ejecting energy generating means, various systems, such as a piezoelectric system, a heating system, and so on, may be employed. However, for arranging a large number of liquid ejecting portions required to be provided mutually independent of each other, at a high density, it is preferred to employ a heater element to heat the liquid to cause the film to boil to eject the liquid from a nozzle opening by a pressure developed by film boiling. Furthermore, it is preferred to employ a structure in which a bubble generated by film boiling is communicated with the ambient air through the nozzle opening.

(7) Furthermore, in the shown embodiment, the bar-code reading process and the like on the probe carrier manufacturer side may be performed manually or automatically using a scanning apparatus, which makes the bar-code reader scan.

In addition, although the so-called bar-code is used as an indicator in the shown embodiment, the present invention is not limited to this configuration. For example, an IC chip or an indicator, which can be identified by means whereby a magnetic form is identified, may be used. Alternatively, a plurality of marks, which have mutually different shapes, may be used.

Moreover, the configuration of the head unit may be a form in which tanks and nozzles are aligned in a line.

When probe tanks on the head unit are changed to manufacture new probe carriers after certain probe carriers are manufactured, it is preferable to clean the nozzles and a solution-providing unit to prevent contamination by the former solution.

Furthermore, storage containers, which can store a plurality of probe tanks, may be arranged such that indicators are located in one plane to control an environment of a storage of the probe solution in the storage container.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications, which fall within the true spirit of the invention.

What is claimed is:

1. A probe carrier manufacturing apparatus comprising:
    ejecting portions for ejecting probe solutions on a carrier to produce a probe carrier, each of the probe solutions containing a probe, which can be specifically coupled with a target substance;
    a plurality of containers for accommodating mutually different probe solutions to be supplied to the ejecting portions, each of the containers individually labeled with an indicator to identify an accommodated probe;
    a container arrangement portion for arranging the plurality of the containers;
    storage means for storing information regarding a sequence of a plurality of indicators, which correspond to the containers arranged on the container arrangement portion;
    reading means for reading the indicators labeled on the plurality of the containers in a predetermined sequence;
    comparing means for comparing the plurality of the indicators read in the predetermined sequence with the information regarding the sequence of the plurality of indicators stored in the storage means; and
    notifying means for notifying a result of a comparison carried out by the comparing means,
    wherein the plurality of the containers are configured to be attachable to and detachable from the ejecting portions.

2. The apparatus according to claim 1, wherein the plurality of the containers are mounted on the ejecting portions.

3. The apparatus according to claim 1, wherein the plurality of the containers are formed in a predetermined arrangement.

4. The apparatus according to claim 1, wherein the indicator is a bar-code.

5. A probe carrier manufacturing apparatus comprising:
    ejecting portions for ejecting probe solutions on a carrier to produce a probe carrier, each of the probe solutions containing a probe, which can be specifically coupled with a target substance;
    a plurality of containers for accommodating mutually different probe solutions to be supplied to the ejecting portions, each of the containers individually labeled with an indicator to identify an accommodated probe;
    storage means for storing information regarding a sequence of indicators corresponding to each of the containers;
    reading means for reading the indicators labeled on the plurality of the containers in a predetermined sequence;
    comparing means for comparing the plurality of the indicators read in the predetermined sequence with the information regarding the sequence of the plurality of indicators stored in the storage means; and
    notifying means for notifying a result of a comparison carried out by the comparing means,
    wherein the plurality of the containers are configured to be attachable to and detachable from the ejecting portions.

6. The apparatus according to claim 5, wherein the plurality of the containers are mounted on the ejecting portions.

7. The apparatus according to claim 5, wherein the plurality of the containers are formed in a predetermined arrangement.

8. The apparatus according to claim 5, wherein the indicator is a bar-code.

9. The apparatus according to claim 5, comprising an ink jet head unit, which includes the ejecting portions and the plurality of the containers.

10. The apparatus according to claim 5, wherein an ejecting portion is structured so that it can be cleaned when a container is exchanged.

11. The apparatus according to claim 5, wherein the container and the ejecting portions are arranged in a line in an ink jet head unit.

12. A method for extracting data on probe carriers using a probe carrier extraction apparatus, each of the probe carriers being labeled with an indicator, the method comprising steps of:

storing indicator information and information relating to each probe carrier labeled with the indicator with correspondence therebetween in a storage device;

receiving information about the indicator from outside; and extracting from the storage device the information relating to the probe carrier corresponding to the information about the indicator received from the outside, wherein the probe carrier is made by applying a plurality of probe solutions to a carrier, wherein extracted information comprises information relating to containers accommodating the probe solutions, wherein the extracted information is container arrangement information, wherein the container arrangement information is information of a sequence of indicators, and wherein the containers are configured to be attachable to and detachable from the ejecting portions.

13. The method according to claim 12, further comprising a step of transmitting at least the indicator information and the information relating to the probe carrier stored in the storage device in response to an externally received demand.

14. The method according to claim 12, further comprising steps of:
    reading the indicator on the probe carrier using a reading device; and
    extracting information relating to the probe carrier corresponding to information about the read indicator from the storage device.

15. The method according to claim 12, wherein the containers are arranged so as to apply accommodated probe solutions to the carrier.

16. The method according to claim 12, wherein the indicator is a bar-code.

17. A probe carrier manufacturing apparatus comprising:
    ejecting portions for ejecting probe solutions on a carrier to produce a probe carrier, each of the probe solutions containing a probe, which can be specifically coupled with a target substance;
    a plurality of containers for accommodating mutually different probe solutions to be supplied to the ejecting portions, each of the containers individually labeled with an indicator to identify an accommodated probe;
    a container arrangement portion for arranging the plurality of the containers;
    storage means for storing information regarding a sequence of a plurality of indicators, which correspond to the containers arranged on the container arrangement portion;
    reading means for reading the indicators labeled on the plurality of the containers in a predetermined sequence;
    comparing means for comparing the plurality of the indicators read in the predetermined sequence with the information regarding the sequence of the plurality of indicators stored in the storage means;
    notifying means for notifying a result of a comparison carried out by the comparing means; and
    an ink jet head unit, which includes the ejecting portions and the plurality of the containers.

18. A probe carrier manufacturing apparatus comprising:
    ejecting portions for ejecting probe solutions on a carrier to produce a probe carrier, each of the probe solutions containing a probe, which can be specifically coupled with a target substance;
    a plurality of containers for accommodating mutually different probe solutions to be supplied to the ejecting portions, each of the containers individually labeled with an indicator to identify an accommodated probe;
    a container arrangement portion for arranging the plurality of the containers;
    storage means for storing information regarding a sequence of a plurality of indicators, which correspond to the containers arranged on the container arrangement portion;
    reading means for reading the indicators labeled on the plurality of the containers in a predetermined sequence;
    comparing means for comparing the plurality of the indicators read in the predetermined sequence with the information regarding the sequence of the plurality of indicators stored in the storage means; and
    notifying means for notifying a result of a comparison carried out by the comparing means,
    wherein an ejecting portion is structured so that it can be cleaned when a container is exchanged.

19. A probe carrier manufacturing apparatus comprising:
    ejecting portions for ejecting probe solutions on a carrier to produce a probe carrier, each of the probe solutions containing a probe, which can be specifically coupled with a target substance;
    a plurality of containers for accommodating mutually different probe solutions to be supplied to the ejecting portions, each of the containers individually labeled with an indicator to identify an accommodated probe;
    a container arrangement portion for arranging the plurality of the containers;
    storage means for storing information regarding a sequence of a plurality of indicators, which correspond to the containers arranged on the container arrangement portion;
    reading means for reading the indicators labeled on the plurality of the containers in a predetermined sequence;
    comparing means for comparing the plurality of the indicators read in the predetermined sequence with the information regarding the sequence of the plurality of indicators stored in the storage means; and
    notifying means for notifying a result of a comparison carried out by the comparing means,
    wherein the container and the ejecting portions are arranged in a line in an ink jet head unit.

* * * * *